(12) United States Patent
Boutell et al.

(10) Patent No.: US 10,351,846 B2
(45) Date of Patent: Jul. 16, 2019

(54) FLEXIBLE TAPE-BASED CHEMISTRY APPARATUS

(71) Applicant: Illumina Cambridge Limited, Essex (GB)

(72) Inventors: Jonathan Mark Boutell, Bishops Stortford (GB); Gary Mark Skinner, Kedington (GB); Gareth Jenkins, New Malden (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 642 days.

(21) Appl. No.: 14/851,090

(22) Filed: Sep. 11, 2015

(65) Prior Publication Data

US 2016/0076025 A1    Mar. 17, 2016

(51) Int. Cl.
*C12N 15/10* (2006.01)
*G01N 33/487* (2006.01)

(52) U.S. Cl.
CPC ..... *C12N 15/1068* (2013.01); *C12N 15/1013* (2013.01); *G01N 33/48764* (2013.01)

(58) Field of Classification Search
None
See application file for complete search history.

(56) References Cited

U.S. PATENT DOCUMENTS

| 5,602,756 | A  | * | 2/1997 | Atwood | B01L 3/50851 165/205 |
| 6,322,971 | B1 | * | 11/2001 | Chetverin | B01J 19/0046 435/6.12 |
| 6,632,653 | B1 | * | 10/2003 | Astle | B01L 3/50853 422/68.1 |
| 8,124,029 | B2 | * | 2/2012 | Polwart | B01L 3/502707 422/502 |
| 8,137,626 | B2 | * | 3/2012 | Maltezos | G01N 21/6452 422/82.07 |
| 2001/0038808 | A1 |   | 11/2001 | Tajima | |
| 2002/0001546 | A1 | * | 1/2002 | Hunter | B01F 13/0071 422/82.05 |
| 2004/0071599 | A1 | * | 4/2004 | Rusch | B01L 3/5085 422/552 |
| 2008/0241938 | A1 |   | 10/2008 | Rea | |
| 2013/0260372 | A1 | * | 10/2013 | Buermann | G01N 21/6428 435/6.1 |
| 2013/0338042 | A1 | * | 12/2013 | Shen | C12Q 1/6848 506/26 |

FOREIGN PATENT DOCUMENTS

| DE | 102004008319 | 9/2005 |
| EP | 1304162 | 4/2003 |
| WO | 200015653 | 3/2000 |
| WO | 2007140294 | 12/2007 |
| WO | 2009054344 | 4/2009 |

* cited by examiner

*Primary Examiner* — Tracy Vivlemore
*Assistant Examiner* — Sahana S Kaup
(74) *Attorney, Agent, or Firm* — Illumina, Inc.

(57) ABSTRACT

An apparatus and method for applying a chemistry to samples of interest are provided. The apparatus and method include a flexible tape mounted on an arrangement of guide rollers. Samples of interest (e.g., clusters of DNA templates) are bound to at least one surface of the flexible tape. The method and apparatus further comprise one or more read heads in relation to the flexible tape and a plurality of reservoirs along a path of the flexible tape. The reservoirs comprise liquids comprising chemical reagents for performing the chemistry on the samples of interest bound to the at least one surface of the flexible tape. The method and apparatus further comprise a drive system for driving at least one of the guide rollers to advance the flexible tape into and out of the reservoirs.

30 Claims, 12 Drawing Sheets

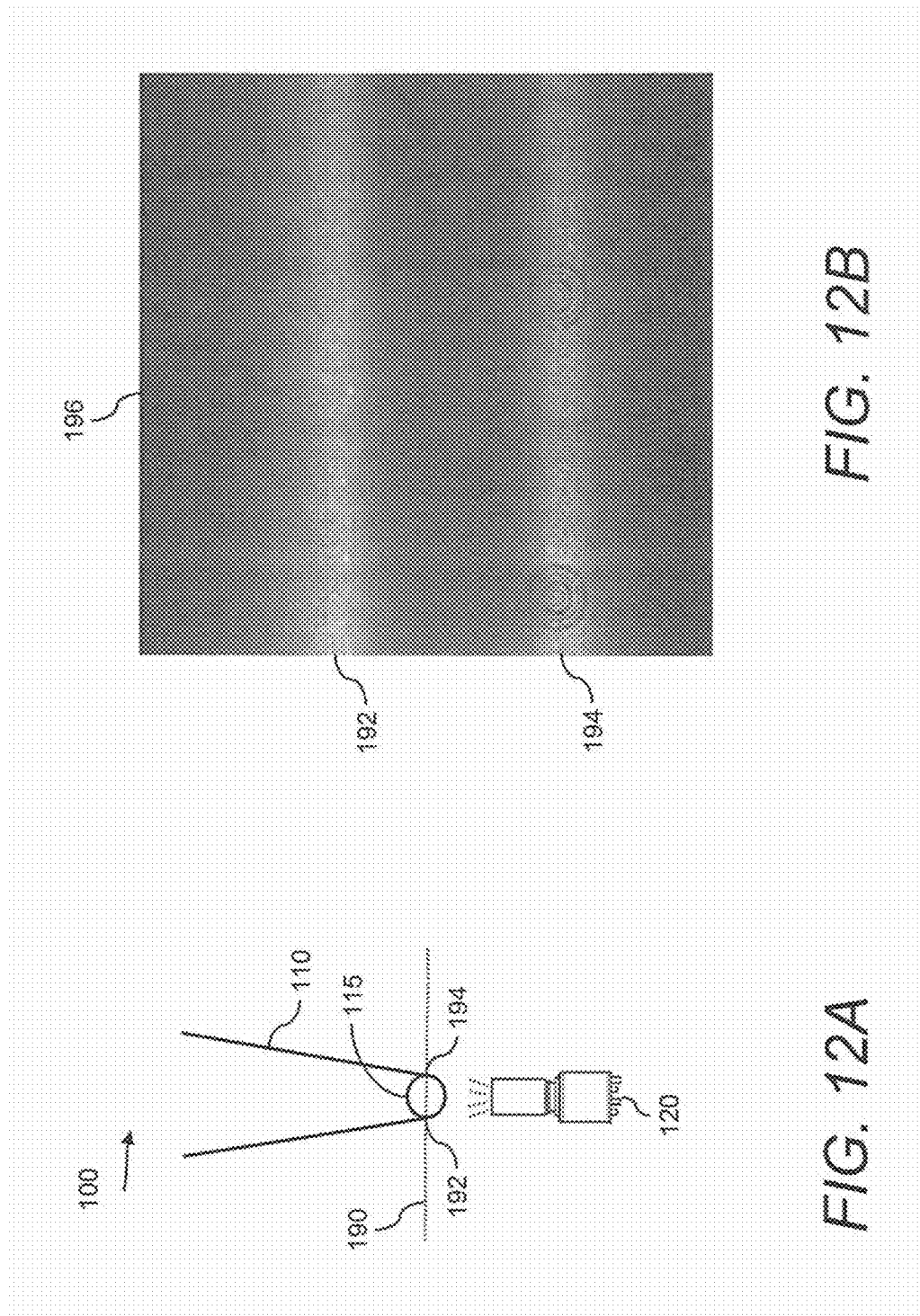

FLEXIBLE TAPE-BASED CHEMISTRY APPARATUS

CROSS-REFERENCE TO RELATED APPLICATIONS

The present application claims the benefit of United Kingdom Patent Application No. 1416422.2, filed on Sep. 17, 2014 and entitled "FLEXIBLE TAPE-BASED CHEMISTRY APPARATUS" which is incorporated herein by reference in its entirety.

BACKGROUND

Embodiments herein relate to compositions, systems and methods for processing chemical reactions, and in particular relates to compositions, systems and methods for DNA sequencing.

Many techniques in modern molecular biology employ synthetic polynucleotides. Some of these techniques include, but are not limited to, DNA sequencing, the polymerase chain reaction (PCR), site directed mutagenesis, whole gene assembly, and single-nucleotide polymorphism (SNP) analysis. Unlike many other reagents used in molecular biology, polynucleotides are not generally available as stock items but are custom made to each user's specification. For example, the sequence, scale, purity, and modifications of a polynucleotide can be specified by the user.

Improvements in polynucleotide synthesis chemistry and processing technology have led to more rapid synthesis at a lower cost. However, polynucleotide synthesis remains a complex, multi-step process that requires a series of high efficiency chemical reactions.

SUMMARY

An apparatus is provided for performing chemistry on samples of interest, comprising: a) a flexible tape mounted on an arrangement of guide rollers, wherein samples of interest (e.g., clusters of DNA templates) are bound to at least one surface of the flexible tape; b) one or more read heads in relation to the flexible tape; c) a plurality of reservoirs along a path of the flexible tape, wherein the reservoirs comprise liquids comprising chemical reagents for performing chemistry on the samples of interest (e.g., DNA sequencing on the DNA templates) bound to at least one surface of the flexible tape; and d) a drive system for driving at least one of the guide rollers whereby the guide rollers advance the flexible tape into and out of individual reservoirs. In one embodiment, the flexible tape mounted on the arrangement of guide rollers comprises a continuous loop configuration. In another embodiment, the flexible tape mounted on the arrangement of guide rollers comprises as reel-to-reel configuration. In a further embodiment, at least one surface of the flexible tape is in direct contact with a flat surface of each of the guide rollers. In another embodiment, the guide rollers comprise sprockets, and wherein the flexible tape comprises sprocket holes along the edges of the flexible tape. In yet another embodiment, the one or more read heads are positioned such that the flexible tape is within a field of view of the read heads and such that a plane of the flexible tape is substantially at the focal plane of the read heads. In another embodiment, the one or more read heads comprise a digital imaging device, particularly a charge-coupled device (CCD) image sensor.

Optionally, the chemistry performed may represent various types of chemistry. Non-limiting examples of chemistry include immunoassays, enzymatic assays, nucleic acid arrays, synthetic chemistry, etc. In general, the tape carries samples of interest that interact with the reagents. The sample of interest on the tap may bind to the reagent, react with the reagent, be cleaved by the reagent, be washed off by the reagent and the like.

In certain embodiments, at least one of the plurality of reservoirs of the apparatus for performing a select chemistry comprises a liquid. For example, the liquid may comprise: an incorporation mix, a wash buffer, a cleavage mix, sample DNA, an kinetic exclusion amplification (KEA) mix, a linearization mix, a linearization denaturation reagent, and/or a sequencing primer. In another embodiment, each of the plurality of reservoirs are moveable and capable of being individually controlled. In yet another embodiment, each of the guide rollers are moveable and capable of being individually controlled. In a further embodiment, at least one read head is arranged downstream of reservoirs comprising sequencing reagents.

In certain embodiments, the flexible tape of the apparatus comprises magnetic tape, plastic tape, or glass. In some embodiments in which the flexible tape comprises magnetic tape, at least one read head is a magnetic read head for writing information to and/or reading information from the flexible tape. In other embodiments, the samples of interest (e.g., clusters of DNA templates) are bound to both sides of the flexible tape, further wherein the apparatus comprises two read heads in which one read head is positioned in relation to one side of the flexible tape and the other read head is positioned in relation to the other side of the flexible tape. In further embodiments, the samples of interest are bound to one side of the flexible tape and the flexible tape comprises a Möbius strip. In still further embodiments, the plurality of reservoirs comprises a carousel of reservoirs capable of rotating from one to another at a given location. In another embodiment, each of the plurality of reservoirs comprises an independently controlled heating element.

A method of DNA template cluster generation is also provided, comprising: a) providing any of the apparatuses disclosed herein; and b) selectively advancing a portion of the flexible tape of the apparatus into a reservoir comprising a liquid comprising sample DNA and a kinetic exclusion amplification (KEA) mix; wherein DNA templates are clustered on a surface of the portion of the flexible tape.

A method of DNA template linearization is also provided, comprising: a) providing any of the apparatuses disclosed herein; and b) selectively advancing a portion of the flexible tape of the apparatus comprising clustered DNA templates on at least one surface of the portion of the flexible tape into reservoirs, wherein the portion of the flexible tape is advanced sequentially into reservoirs comprising: i) a linearization mix; ii) a linearization denaturation reagent; and iii) a sequencing primer; wherein DNA templates on a surface of the portion of the flexible tape are linearized.

A method of sequencing DNA clusters is also provided, comprising: a) providing any of the apparatuses disclosed herein; and b) selectively advancing a portion of the flexible tape of the apparatus comprising clustered DNA templates on at least one surface of the portion of the flexible tape into reservoirs, wherein the portion of the flexible tape is advanced sequentially into reservoirs comprising: i) an incorporation mix; ii) a wash buffer; iii) a cleavage mix; and iv) a wash buffer; wherein between steps b(ii) and b(iii), the portion of the flexible tape comprising clustered DNA templates is passed by the field of view of a read head, wherein images of the DNA clusters are captured and sequencing information is obtained.

BRIEF DESCRIPTION OF THE DRAWINGS

FIG. 12A illustrates a plan view of an example of a read head configuration of the flexible tape-based chemistry apparatus in accordance with embodiments herein; and FIG. 12B shows an example of an image captured by the read head configuration shown in FIG. 12A in accordance with embodiments herein.

DETAILED DESCRIPTION

Figure 1:
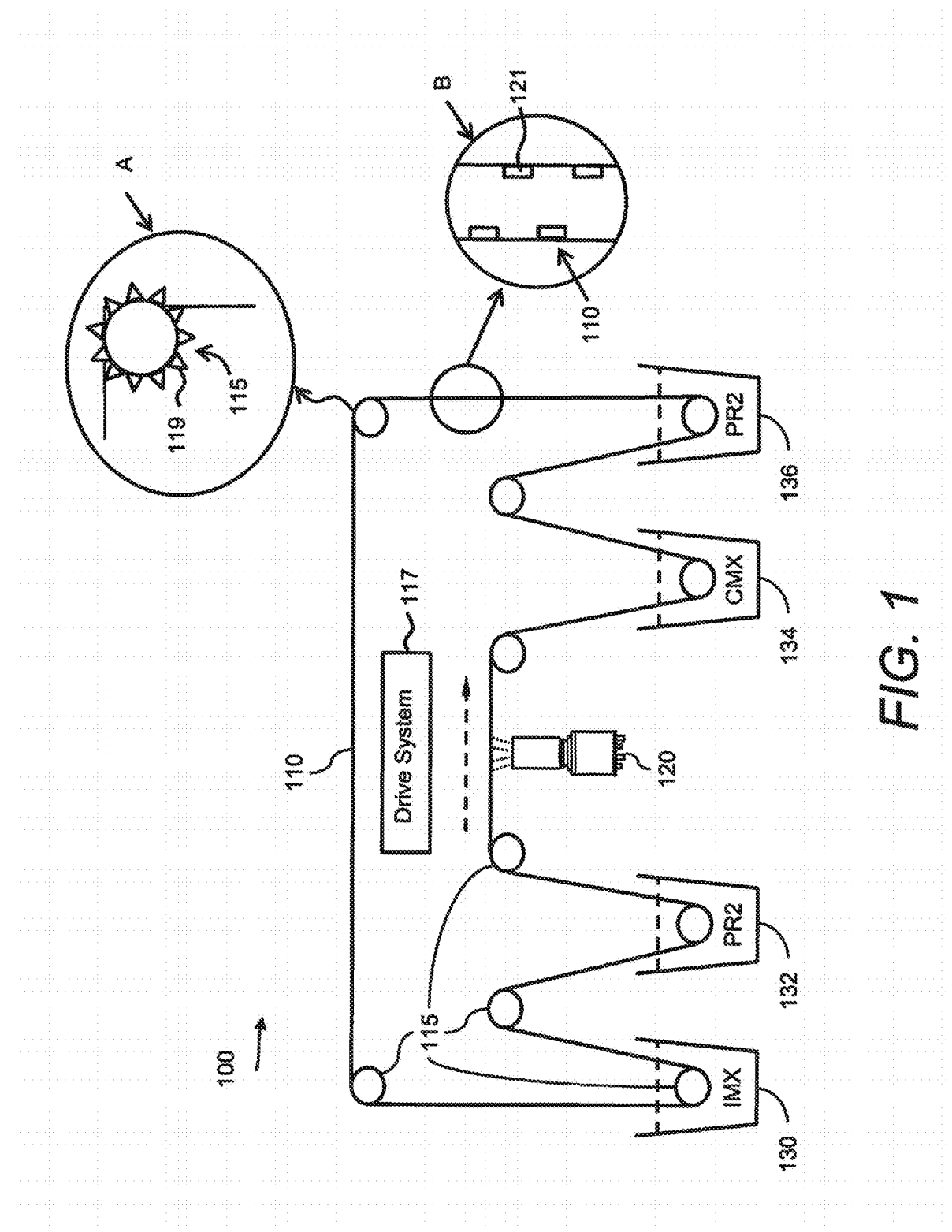
FIG. 1 illustrates a plan view of an example of a simple flexible tape-based chemistry apparatus in a continuous loop configuration in accordance with embodiments herein.

As used herein, the following terms have the meanings indicated.

The term "flexible tape" as described herein is a type of solid support that comprises two exterior edges and two surfaces opposite one another. The flexible tape can be adapted to be moved or advanced by a variety of methods. For example, the flexible tape can be advanced by engaging one or more surfaces of the flexible tape with a device, such as a roller, that produces friction when engaged with a surface of the flexible tape. In some embodiments, at least one edge of the flexible tape can be adapted to contact a member for moving the flexible tape. In some embodiments, an edge of a flexible tape can be adapted to contact a guide roller, for example, the edge can include perforations or indentations that mesh with a guide roller that moves the flexible tape. Other methods of moving the flexible tape that are known in the art, for example, manipulation with a turn table or manipulation with a robotic arm, are also contemplated herein.

A variety of sequencing reagents may be utilized within the apparatuses and methods described herein. For example, a suitable reagent solution for incorporation of nucleotides is referred to as an "incorporation mix" and contains an incorporation buffer (50 mM Tris-HCl pH 8.0, 6 mM $MgSO_4$, 1 mM EDTA, 0.05% (v/v) Tween-20, 50 mM NaCl) plus 110 nM YAV exo-C223S, and 1 M each of the four types of, optionally labelled, nucleotides. Similarly, a suitable "wash buffer" contains 0.3× SSC containing 0.1% Tween-20. A suitable reagent for denaturation is a "denaturation reagent" and contains urea, hydroxide or formamide or other similar reagent.

The term "chemical cleavage" encompasses any method which utilises a non-nucleic acid and non-enzymatic chemical reagent in order to promote/achieve cleavage of one or both strands of a template polynucleotide duplex. If required, one or both strands of a template polynucleotide duplex may include one or more non-nucleotide chemical moieties and/or non-natural nucleotides and/or non-natural backbone linkages in order to permit a chemical cleavage reaction. In some embodiments, the modification(s) required to permit chemical cleavage may be incorporated into an amplification primer used to form the template polynucleotide duplex by solid-phase nucleic acid amplification. A suitable reagent solution for cleavage of polynucleotides is referred to as a "cleavage mix" and contains 100 mM Tris (2-carboxyethyl)-phosphate hydrochloride (TCEP), 100 mM Tris pH 9.0, 100 mM NaCl, 50 mM sodium ascorbate, and 0.05% Tween 20.

The term "linearization" refers to the selective removal of a complementary DNA template strand. A suitable reagent solution for linearization is a "linearization mix" and contains 1429 uL of water, 64 mg of sodium periodate, 1500 μL of formamide, 60 μL of 1M Tris pH8, and 6011.4 μL of 3-aminopropanol (for a final volume of 3 mL). The periodate is first mixed with the water while the Tris is mixed with the formamide. The two solutions are then mixed together and the 3-aminopropanol is added to that mixture.

The term "amplifying" as used herein is intended to mean the process of increasing the numbers of a template polynucleotide sequence by producing one or more copies. Accordingly it will be clear that the amplification process can be either exponential or linear. In exponential amplification the number of copies made of the template polynucleotide sequence increases at an exponential rate. For example, in an ideal PCR reaction with 30 cycles, 2 copies of template DNA will yield $2^{30}$ or 1,073,741,824 copies. In linear amplification the number of copies made of the template polynucleotide sequences increases at a linear rate. For example, in an ideal 4-hour linear amplification reaction whose copying rate is 2000 copies per minute, one molecule of template DNA will yield 480,000 copies.

The term "amplification cycle" refers to one or more steps of an amplification process that are sufficient to produce one or more copies of a nucleic acid template. By way of example, an amplification cycle includes providing one or more nucleic acid templates, denaturing the nucleic acid templates to produce single stranded nucleic acid templates, annealing one or more primers to the single stranded nucleic acid templates, and extending the primers to produce copies of the single stranded nucleic acid templates. Thus, a cycle of amplification can include a unit of one or more steps that is repeated in a round of amplification.

The nucleotides used in the amplification process may be ribo- or deoxyribo-nucleotides. The nucleotides used in the amplification may be nucleotide 5' polyphosphates, for example 5'triphosphates. The nucleotides used in the amplification reaction may be the four nucleotide triphosphates typically found in native DNA: dATP, dGTP, dCTP and dTTP.

As used herein, the terms high, higher, increase(s), increased, or increasing refer to any increase above a reference or control, unless stated otherwise. The terms low, lower, decrease(s), decreased, decreasing, reduce(s), reduced, reducing or reduction refer to any decrease below a reference or control, unless stated otherwise. By way of example, a control includes control values or control levels, which can be values or levels prior to, or in the absence of, a stimulus. A control or control value includes the level of efficiency of amplification of nucleic acid sequences under standard amplification conditions or can comprise a known value, level or standard. Thus, for example, a higher or lower value (e.g., temperature or concentration) as compared to a control refers to a value that is higher or lower than a known or arbitrarily set value.

The term "copy" when used in reference to a first nucleic acid molecule is intended to mean a second nucleic acid molecule having the same sequence as the first nucleic acid or the complementary sequence of the nucleic acid. The nucleic acids can be single stranded or double stranded. For example, a single stranded copy can have the same sequence of a single stranded template, a single stranded copy can have the complementary sequence of a single stranded template, a double stranded copy can include the same sequence and the complementary sequence (i.e. two strands) of a single stranded template, or a double stranded copy can include the same sequences as a double stranded template. Similarly, the term "copy" when used in reference to a nucleic acid sequence means the same sequence or the complementary sequence.

As used herein, the terms "polynucleotide", "oligonucleotide" or "nucleic acid" can refer to deoxyribonucleic acid (DNA), ribonucleic acid (RNA) or analogues of either DNA or RNA made, for example, from nucleotide analogues. The terms "polynucleotide", "oligonucleotide" or "nucleic acid" are applicable to single stranded (such as sense or antisense) and double stranded molecules. The terms "polynucleotide", "oligonucleotide" or "nucleic acid" as used herein also encompass cDNA, that is complementary or copy DNA produced from an RNA template, for example by the action of reverse transcriptase.

Single stranded polynucleotide molecules useful in a method or composition, as described herein, may have originated in single-stranded form, as DNA or RNA or may have originated in double-stranded DNA (dsDNA) form (e.g. genomic DNA fragments, PCR and amplification products and the like). Thus a single stranded polynucleotide may be the sense or antisense strand of a polynucleotide duplex. Methods of preparation of single stranded polynucleotide molecules suitable for use in the methods herein using standard techniques are well known in the art.

The term "immobilized" or "bound" as used herein is intended to encompass direct or indirect, covalent or non-covalent attachment, unless indicated otherwise, either explicitly or by context. In certain embodiments herein, covalent attachment may be preferred, but generally all that is required is that the molecules (e.g. nucleic acids) remain immobilized or attached to a support under conditions in which it is intended to use the support, for example in applications requiring nucleic acid amplification and/or sequencing.

Primer oligonucleotides or primers are polynucleotide sequences that are capable of annealing specifically to one or more single stranded polynucleotide template to be amplified under conditions encountered in the primer annealing step of each cycle of an amplification reaction. Generally amplification reactions can use at least two amplification primers, often denoted "forward" and "reverse" primers. In certain embodiments the forward and reverse primers may be identical. The forward primer oligonucleotides can include a "template-specific portion", being a sequence of nucleotides capable of annealing to a primer-binding sequence in at least one strand of the molecule to be amplified. Reverse primer oligonucleotides can include a template specific portion capable of annealing to the complement of the strand to which the forward primer anneals during the annealing step. Generally primer oligonucleotides are single stranded polynucleotide structures. They may also contain a mixture of natural and non-natural bases and also natural and non-natural backbone linkages, provided that any non-natural modifications do not preclude function as a primer—that being defined as the ability to anneal to a template polynucleotide strand during conditions of the amplification reaction and to act as an initiation point for synthesis of a new polynucleotide strand complementary to the template strand.

Primers may additionally comprise non-nucleotide chemical modifications, again provided that such modifications do not permanently prevent primer function. Chemical modifications may, for example, facilitate covalent attachment of the primer to a solid support. Certain chemical modifications may themselves improve the function of the molecule as a primer, or may provide some other useful functionality, such as providing a site for cleavage to enable the primer (or an extended polynucleotide strand derived therefrom) to be cleaved from a solid support.

Although embodiments are described that may encompass solid-phase amplification methods, in which only one amplification primer is immobilized on a solid support (the other primer usually being present in free solution), in a particular embodiment, the solid support may be provided with both the forward and reverse primers immobilized. In practice there can be a plurality of identical forward primers and/or a plurality of identical reverse primers immobilized on the solid support, for example, in embodiments wherein the amplification process utilizes an excess of primers to sustain amplification. Thus references herein to forward and reverse primers are to be interpreted accordingly as encompassing a plurality of such primers unless the context indicates otherwise.

"Solid-phase amplification" as used herein refers to any nucleic acid amplification reaction carried out on or in association with a solid support such that all or a portion of the amplified products are immobilized on the solid support. In particular, the term encompasses solid phase amplification reactions analogous to standard solution phase PCR except that one or both of the forward and reverse amplification primers is/are immobilized on the solid support.

Primer oligonucleotides and single stranded polynucleotide molecules that have been immobilized on a solid support at a desired density can be used to generate extension products by carrying out an appropriate number of cycles of amplification on the covalently bound single stranded polynucleotide molecules so that each colony, or cluster comprises multiple copies of the original immobilized single stranded polynucleotide molecule (and its complementary sequence). One cycle of amplification can include steps of hybridization, extension and denaturation. Such steps are generally comparable with the steps of hybridization, extension and denaturation of PCR.

In embodiments utilizing solid phase amplification, suitable conditions can be applied to a single stranded polynucleotide molecule and a plurality of immobilized primer oligonucleotides such that sequence Z at the 3' end of the single stranded polynucleotide molecule hybridizes to a primer oligonucleotide sequence X to form a complex wherein, the primer oligonucleotide hybridizes to the single stranded template to create a "bridge" structure. Suitable conditions such as neutralizing and/or hybridizing buffers are well known in the art (See Sambrook et al., Molecular Cloning, A Laboratory Manual, $3^{rd}$ Ed, Cold Spring Harbor Laboratory Press, NY; Current Protocols, eds Ausubel et al.). The neutralizing and/or hybridizing buffer may then be removed. One suitable hybridization buffer is referred to as "amplification pre-mix", and contains 2 M Betaine, 20 mM Tris, 10 mM Ammonium Sulfate, 2 mM Magnesium sulfate, 0.1% Triton, 1.3% DMSO, pH 8.8.

By applying suitable conditions, an extension reaction can be performed for a complex formed between immobilized primer and single stranded polynucleotide template. The primer oligonucleotide of the complex can be extended by sequential addition of nucleotides to generate an extension product complementary to the single stranded polynucleotide molecule.

Examples of enzymes with polymerase activity, which can be used in the methods and systems described herein, are DNA polymerase (Klenow fragment, T4 DNA polymerase, Bst polymerase), heat-stable DNA polymerases from a variety of thermostable bacteria (such as Taq, VENT, Pfu, Tfl, Phusion DNA polymerases) as well as their genetically modified derivatives (TaqGold, VENTexo, Pfu exo). A combination of RNA polymerase and reverse transcriptase can also be used to generate the extension products. A useful polymerase enzyme can have strand displacement activity. The polymerase enzyme can be active at a pH of about 7 to about 9, particularly pH 7.9 to pH 8.8. The nucleoside triphosphate molecules used can be deoxyribonucleotide triphosphates, for example dATP, dTTP, dCTP, dGTP, or they can be ribonucleoside triphosphates for example ATP, UTP, CTP, GTP. The nucleoside triphosphate molecules may be naturally or non-naturally occurring. An amplification reaction may also contain additives such as DMSO and or Betaine, for example, to normalise the melting temperatures of the different sequences in the template strands. A suitable solution for initial cycles of extension is referred to as "amplification mix" and contains 2 M betaine, 20 mM Tris, 10 mM Ammonium Sulfate, 2 mM Magnesium sulfate, 0.1% Triton, 1.3% DMSO, pH 8.8 plus 200 mM dNTPs and 80 units/mL of Bst polymerase (NEB Product ref M0275L).

The denaturation can be carried out using heat or by using a denaturing buffer. Suitable denaturing buffers are well known in the art (See Sambrook et al., Molecular Cloning, A Laboratory Manual, $3^{rd}$ Ed, Cold Spring Harbor Laboratory Press, NY; Current Protocols, eds. Ausubel et al.). By way of example it is known that alterations in pH and low ionic strength solutions can denature nucleic acids at substantially isothermal temperatures. Formamide and urea can be used for denaturation. In a particular embodiment the concentration of formamide is 50% or more, and may be used neat. Such conditions result in denaturation of double stranded nucleic acid molecules to single stranded nucleic acid molecules. Alternatively or additionally, the strands may be separated by treatment with a solution of very low salt (for example less than 0.1 mM cationic conditions) and high pH (>12) or by using a chaotropic salt (e.g. guanidinium hydrochloride). In a particular embodiment, a strong base may be used. A strong base is a basic chemical compound that is able to deprotonate very weak acids in an acid base reaction. The strength of a base is indicated by its $pK_b$ value. Compounds with a $pK_b$ value of less than about 1 are called strong bases and are well known to a skilled practitioner. In a particular embodiment the strong base is Sodium Hydroxide (NaOH) solution used at a concentration of from 0.05 M to 0.25 M. More particularly NaOH is used at a concentration of 0.1 M.

It may be advantageous to perform optional washing steps in between steps of an amplification method. For example, an extension buffer without polymerase enzyme with or without dNTPs could be applied to a solid support upon which amplification is being carried out and it can be applied before being removed and replaced with complete extension buffer (extension buffer that includes all necessary components for extension to proceed).

Multiple cycles of amplification on a solid surface under conditions exemplified above can result in a nucleic acid colony or "cluster" comprising multiple immobilized copies of a particular single stranded polynucleotide sequence and its complementary sequence. Initial immobilization of a single stranded polynucleotide molecule under conditions exemplified herein can result in the single stranded polynucleotide molecule only hybridizing with primer oligonucleotides located at a distance within the total length of the single stranded polynucleotide molecule. Thus, the boundary of the nucleic acid colony or cluster formed can be limited to a relatively local area, namely the area in which the initial single stranded polynucleotide molecule was immobilized. If conditions are used wherein the templates and the complementary copies thereof remain immobilized throughout the whole amplification process, then the templates do not become intermingled other than by becoming large enough to overlap on the surface. In particular embodiments, there is no non-immobilized nucleic acid during any part of the amplification process, and thus the templates cannot diffuse and initiate further clusters elsewhere on the surface.

An amplification process may entail cycles of exposure to conditions for hybridization, extension and denaturation of nucleic acid sequences. The cycles may be repeated in order to obtain a sufficient level of amplification. The amplification process (e.g., in a round) may be carried using, for example, 10, 15, 20, 25, 30, 35, 40 or 45 or more cycles of amplification. Each cycle may be carried out using the same reagents and conditions, or the reagents and/or conditions may be varied between different cycles. For example, the first 5, 10, 15, 20 or 25 cycles, in a first round, may be carried out using extension conditions with equimolar concentrations of four different nucleotide types, and subsequent cycles, in a second round, may be carried out using conditions resulting in less efficiently incorporated nucleotides. Normalized amplification conditions using less efficiently incorporated nucleotides can be used. An increased number of amplification cycles can be carried out, as the overall efficiency of amplification is reduced, and the AT rich sequences do not become over-amplified. It is therefore possible to carry out, for example, 25 cycles of amplification in a first round using equimolar nucleotide concentrations, and 15 or more additional cycles of amplification in a second round using conditions using nucleotides incorporated with lower efficiency (for example limited concentrations of A and/or T nucleotides). Such additional cycles in the second round amplify the GC rich clusters preferentially to the AT rich clusters, hence normalizing the intensity of clusters of different sequence compositions.

Hybridization, extension and denaturation steps of an amplification method set forth herein may all be carried out at the same, substantially isothermal temperature. Preferably the temperature is from 37° C. to about 75° C., depending on the choice of enzyme, more preferably from 50° C. to 70° C., yet more preferably from 60° C. to 65° C. for Bst polymerase. In a particular embodiment the substantially isothermal temperature may be around the melting temperature of the oligonucleotide primer(s). Methods of calculating appropriate melting temperatures are known in the art. For example the annealing temperature may be about 5° C. below the melting temperature (Tm) of the oligonucleotide primers. In yet another particular embodiment the substantially isothermal temperature may be determined empirically. The temperature can be that at which the oligonucleotide displays greatest specificity for the primer binding site whilst reducing non-specific binding.

Embodiments are described for a flexible tape-based chemistry apparatuses for performing DNA chemistry, such as, but not limited to, DNA cluster generation and sequencing. In one embodiment, the flexible tape-based chemistry apparatus uses a continuous loop configuration for advancing the flexible tape. In another embodiment, the flexible tape-based chemistry apparatus uses a reel-to-reel configuration for advancing the flexible tape. Certain reagents are provided along the path of the flexible tape, whereby the flexible tape may pass selectively in and out of the reagents. In one example of the flexible tape-based chemistry apparatus, there is a cluster generation mode of operation, a read preparation mode of operation, and a sequencing mode of operation.

Optionally, the chemistry performed may represent various types of chemistry. Non-limiting examples of chemistry include immunoassays, enzymatic assays, nucleic acid arrays, synthetic chemistry, etc. In general, the tape carries samples of interest that interact with the reagents. The sample of interest on the tap may bind to the reagent, react with the reagent, be cleaved by the reagent, be washed off by the reagent and the like.

FIG. 1 illustrates a plan view of an example of a simple flexible tape-based chemistry apparatus 100 in a continuous loop configuration. In this example, flexible tape-based chemistry apparatus 100 includes a fixed length of flexible tape 110 mounted on an arrangement of guide wheels or guide rollers 115. Flexible tape-based chemistry apparatus 100 also includes a drive system for driving at least one of the guide rollers 115 for advancing flexible tape 110 around the loop. Flexible tape 110 can be, for example, standard magnetic tape, flexible plastic tape, flexible glass, and the like. In one example, the surface of flexible tape 110 rides directly on the flat surface of guide rollers 115. Optionally, in a preferred example, guide rollers 115 are gears so that flexible tape 110 is progressed without guide rollers 115 contacting the front surface—like an old fashioned film strip or a camera roll, an example of which is shown in FIG. 1 in detail areas A and B. In this example, guide rollers 115 have sprockets 119 that can be engaged with corresponding sprocket holes 121 along the edges of flexible tape 110. Accordingly, the surface of flexible tape 110 can be out of contact with the surface of guide rollers 115, which may be beneficial in the operations of flexible tape-based chemistry apparatus 100. Optionally, some guide rollers 115 can be formed as non-gear standard rollers and others can be gears. For example, if chemistry is being performed on one side, the bottom guide rollers 115 can be standard rollers because they are contacting the back, and the top guide rollers 115 can be gears because they are contacting the top. Using the drive system 117, flexible tape 110 can be advanced along guide rollers 115 at any speed and in any direction.

A read head 120 is provided in relation to flexible tape 110 and in relation to guide rollers 115. Read head 120 can be a digital imaging device, such as a charge-coupled device (CCD) image sensor. Read head 120 is positioned such that flexible tape 110 is within its field of view and such that the plane of flexible tape 110 is substantially at the focal plane of read head 120. Flexible tape-based chemistry apparatus 100 is not limited to one read head 120 only. Flexible tape-based chemistry apparatus 100 can include two or more read heads 120. Chemistry can occur on one or both sides of flexible tape 110. For example, flexible tape-based chemistry apparatus 100 can include two read heads 120 or just one read head 120 wherein one side is read, then flexible tape 110 is flipped to read the other side.

A plurality of reservoirs is provided along flexible tape 110 and in relation to certain guide rollers 115. The reservoirs hold certain liquids for processing a sample of interest such as in a DNA sequencing operation. Namely, chemical reactions take place within the reservoirs. For example, flexible tape-based chemistry apparatus 100 includes, in order, a reservoir 130, a reservoir 132, a reservoir 134, and a reservoir 136. Reservoirs 130, 132, 134, 136 are provided in relation to respective guide rollers 115 so that flexible tape 110 can pass in and out of the individual reservoirs 130, 132, 134, 136 as shown.

In one example, reservoirs 130 and 132 hold certain sequencing reagents. For example, reservoir 130 is loaded with an incorporation mix (IMX) and reservoir 132 is loaded with a wash buffer (PR2). Further, reservoir 134 is loaded with a cleavage mix (CMX) and reservoir 136 is also loaded with PR2. If reservoirs 130, 132, 134, 136 are provided in order and the movement of flexible tape 110 is in the direction from reservoir 130 toward reservoir 136, read head 120 is arranged between reservoir 132 and reservoir 134 as shown. Namely, read head 120 is arranged downstream of reservoirs 130 and 132 and upstream of reservoirs 134 and 136.

Sample generation (e.g. Cluster generation or clustering in sequencing) is the amplification of the DNA template to create hundreds of copies of the template in dense clusters. With respect to flexible tape-based chemistry apparatus 100, the clusters (not shown) are bound to one or both surfaces of flexible tape 110. In operation, clusters are provided on at least one surface of flexible tape 110. Flexible tape 110 is advanced so that the clusters pass through the IMX in reservoir 130 with a certain speed and/or dwell time. Next, flexible tape 110 is advanced so that the clusters pass through the PR2 in reservoir 132 with a certain speed and/or dwell time. Next, flexible tape 110 is advanced so that the clusters pass into the field of view of read head 120. Using read head 120, images of the clusters are captured and sequencing information is obtained. Next, flexible tape 110 is advanced so that the clusters pass through the CMX in reservoir 134 with a certain speed and/or dwell time. Next, flexible tape 110 is advanced so that the clusters pass through the PR2 in reservoir 136 with a certain speed and/or dwell time and one pass of the sequencing process is complete. Flexible tape 110 may loop multiple times through reservoirs 130, 132, 134, 136 and readings captured by read head 120 with each loop.

The drive system (not shown) can provide variable speed so that, for example, the dwell time in one reservoir can be 5 sec while the dwell time in another reservoir can be 20 sec. However, another way to achieve different dwell times for different reagents is to provide varying geometries of the reservoirs, wherein the different reservoirs have different path lengths. In so doing, differing dwell times are achieved while maintaining a constant drive speed, which may be beneficial, for example, when scanning the entire length of flexible tape 110 and when there is a desire for the scan speed to be held constant throughout the entire scan cycle.

Figure 2:
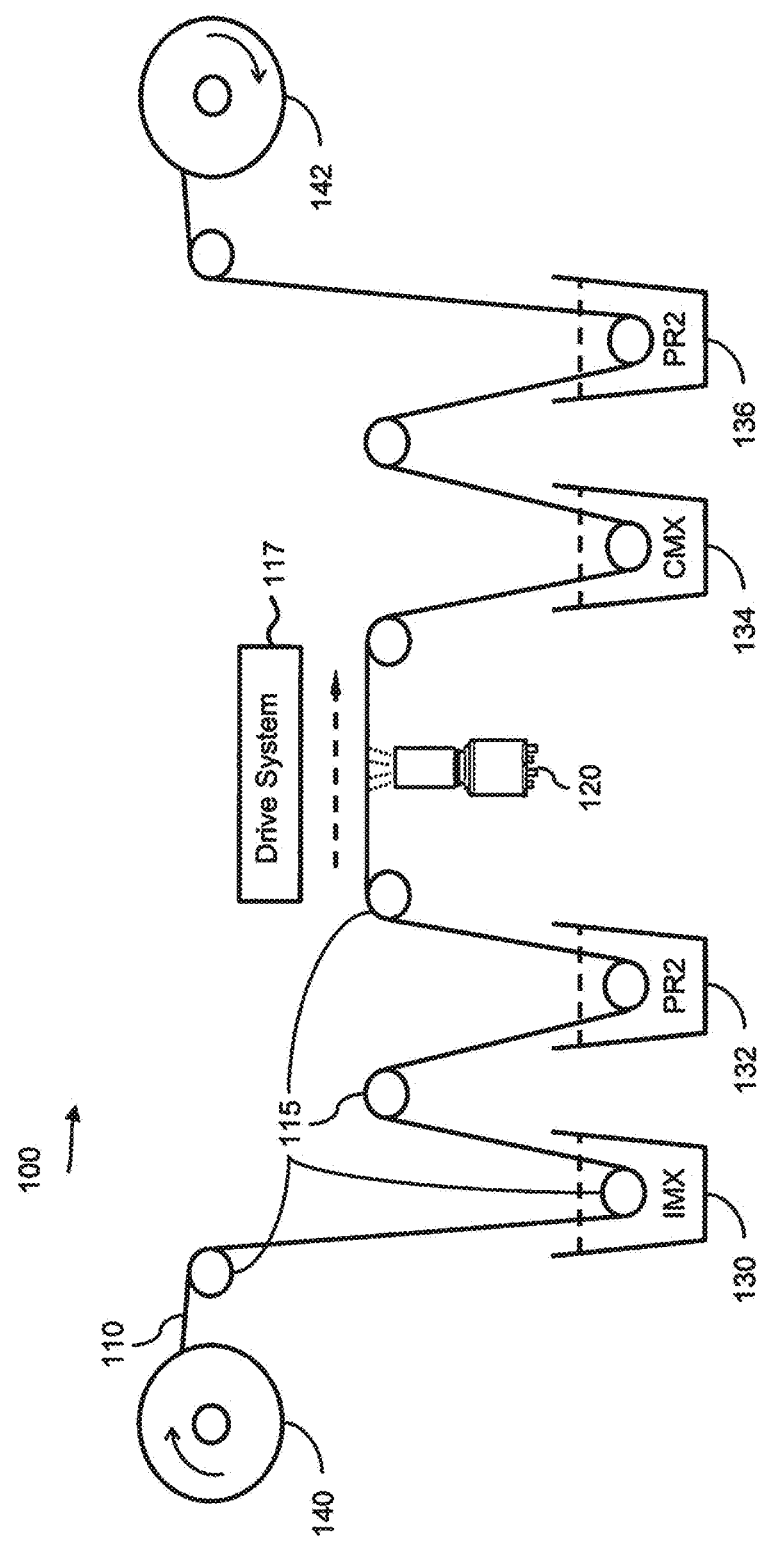
FIG. 2 illustrates a plan view of an example of a simple flexible tape-based chemistry apparatus in a reel-to-reel configuration in accordance with embodiments herein.

FIG. 2 illustrates a plan view of an example of the flexible tape-based chemistry apparatus 100, but in a reel-to-reel configuration instead of a continuous loop configuration. The flexible tape-based chemistry apparatus 100 shown in FIG. 2 is substantially the same as flexible tape-based chemistry apparatus 100 shown in FIG. 1 except that it includes a payout reel 140 and a take-up reel 142. In this example, a supply of flexible tape 110 is provided on payout reel 140 at the input of flexible tape-based chemistry apparatus 100. The processed flexible tape 110 is collected on take-up reel 142 at the output of flexible tape-based chemistry apparatus 100. In this example, the drive system (not shown) is driving payout reel 140 and/or take-up reel 142, whereby flexible tape 110 can be advanced along guide rollers 115 at any speed and in any direction.

Figure 3:
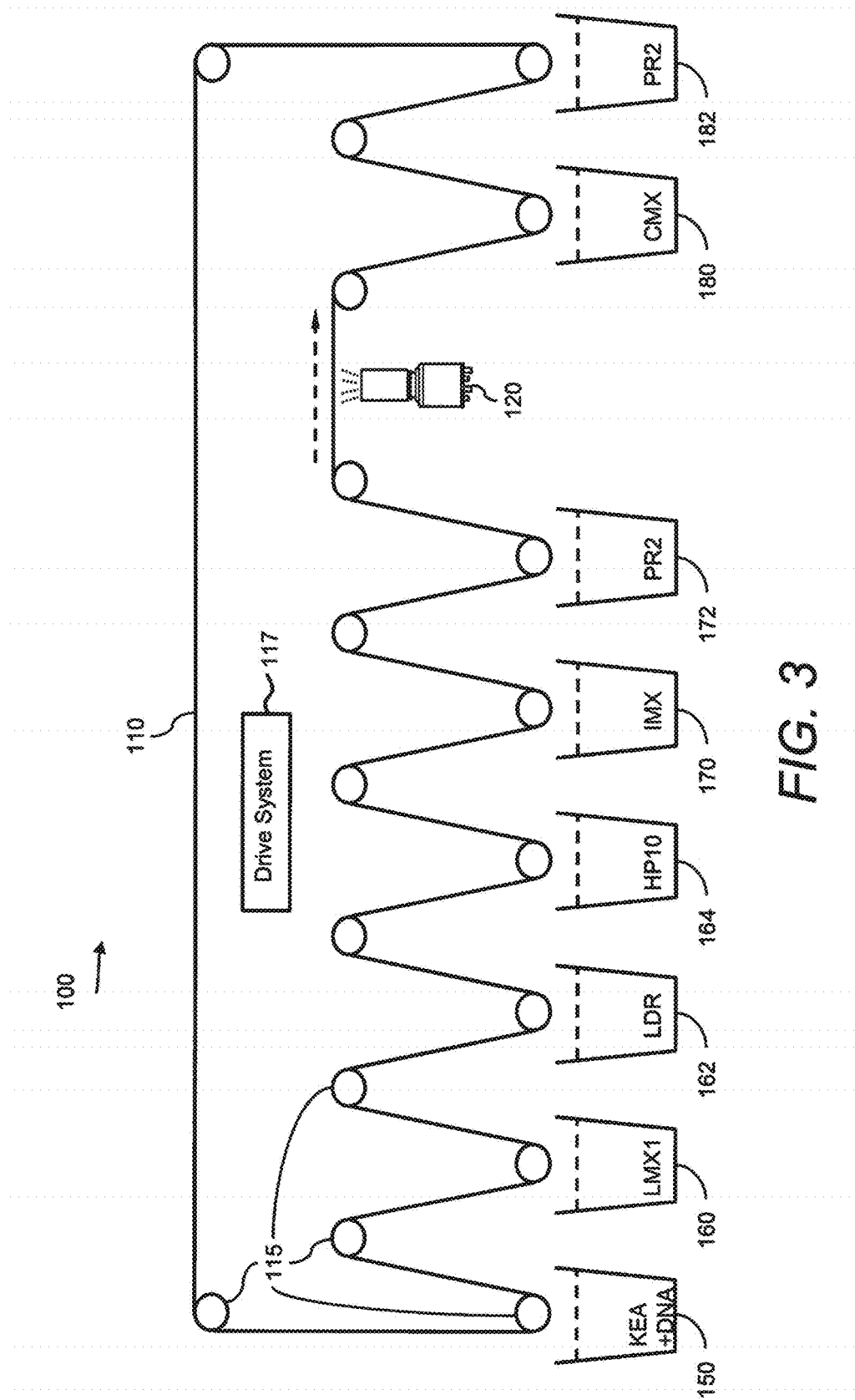
FIG. 3 illustrates plan views of another example of the flexible tape-based chemistry apparatus in a continuous loop configuration in accordance with embodiments herein.
Figure 4:
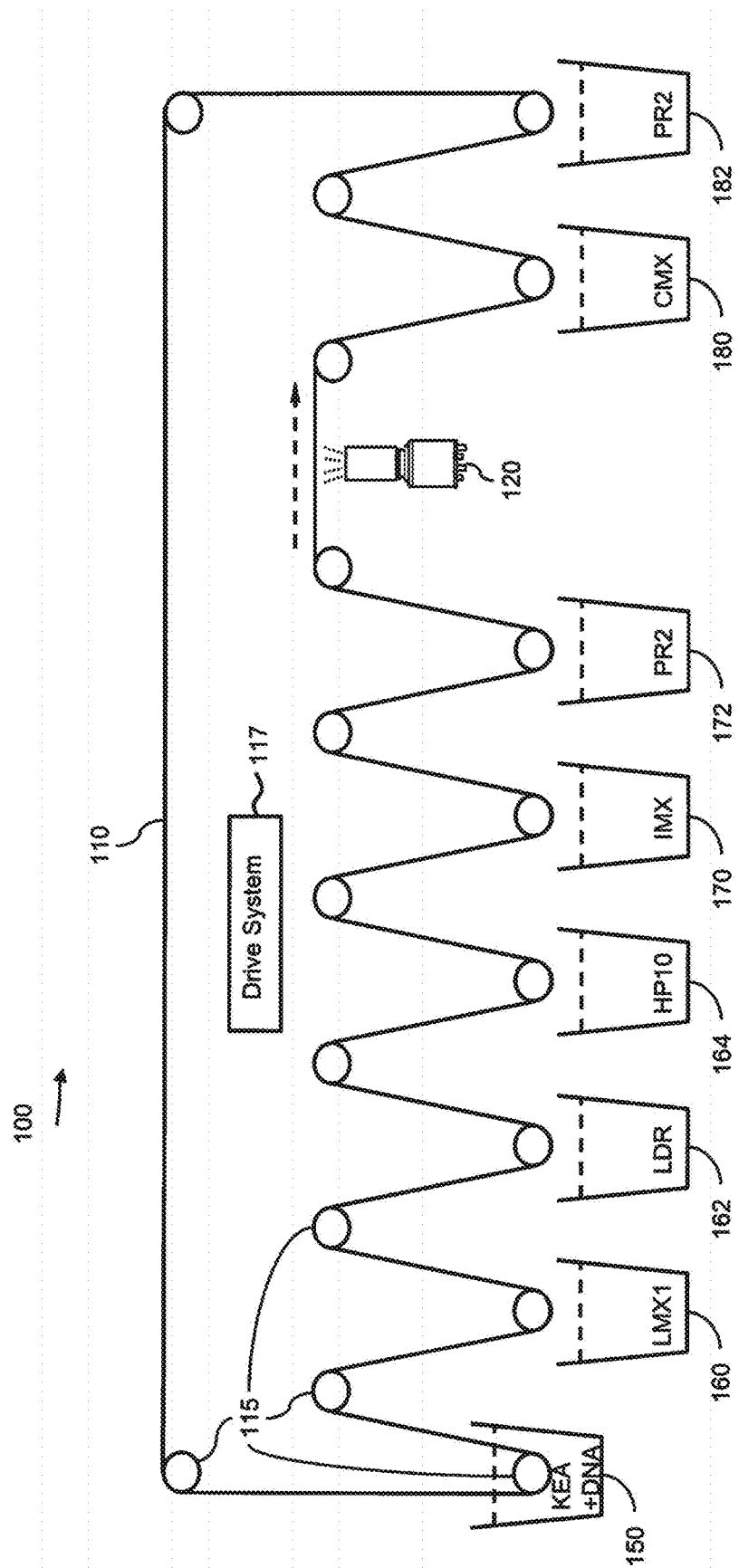
FIG. 4 illustrates plan views of another example of the flexible tape-based chemistry apparatus in a continuous loop configuration in accordance with embodiments herein.
Figure 5:
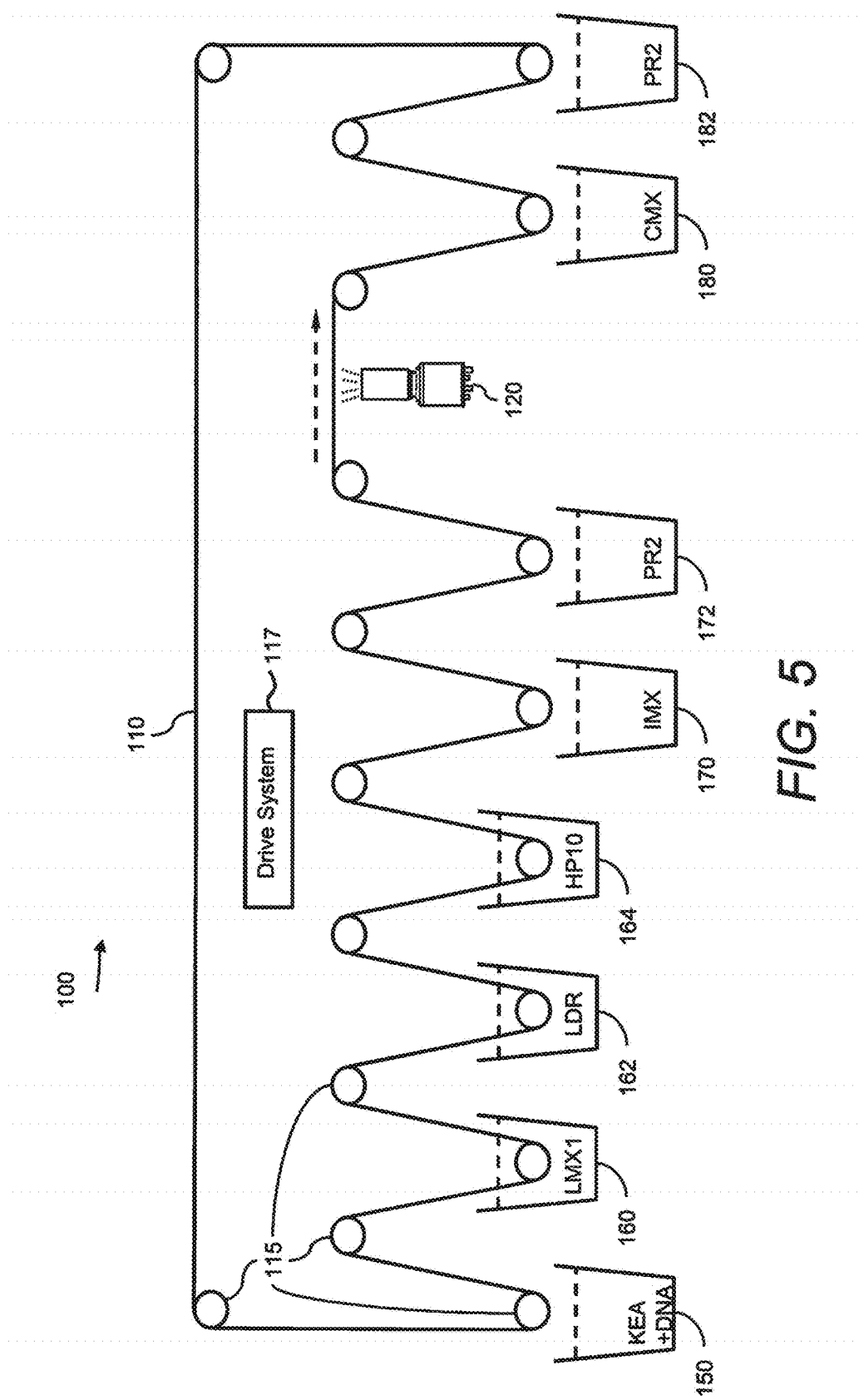
FIG. 5 illustrates plan views of another example of the flexible tape-based chemistry apparatus in a continuous loop configuration in accordance with embodiments herein.
Figure 6:
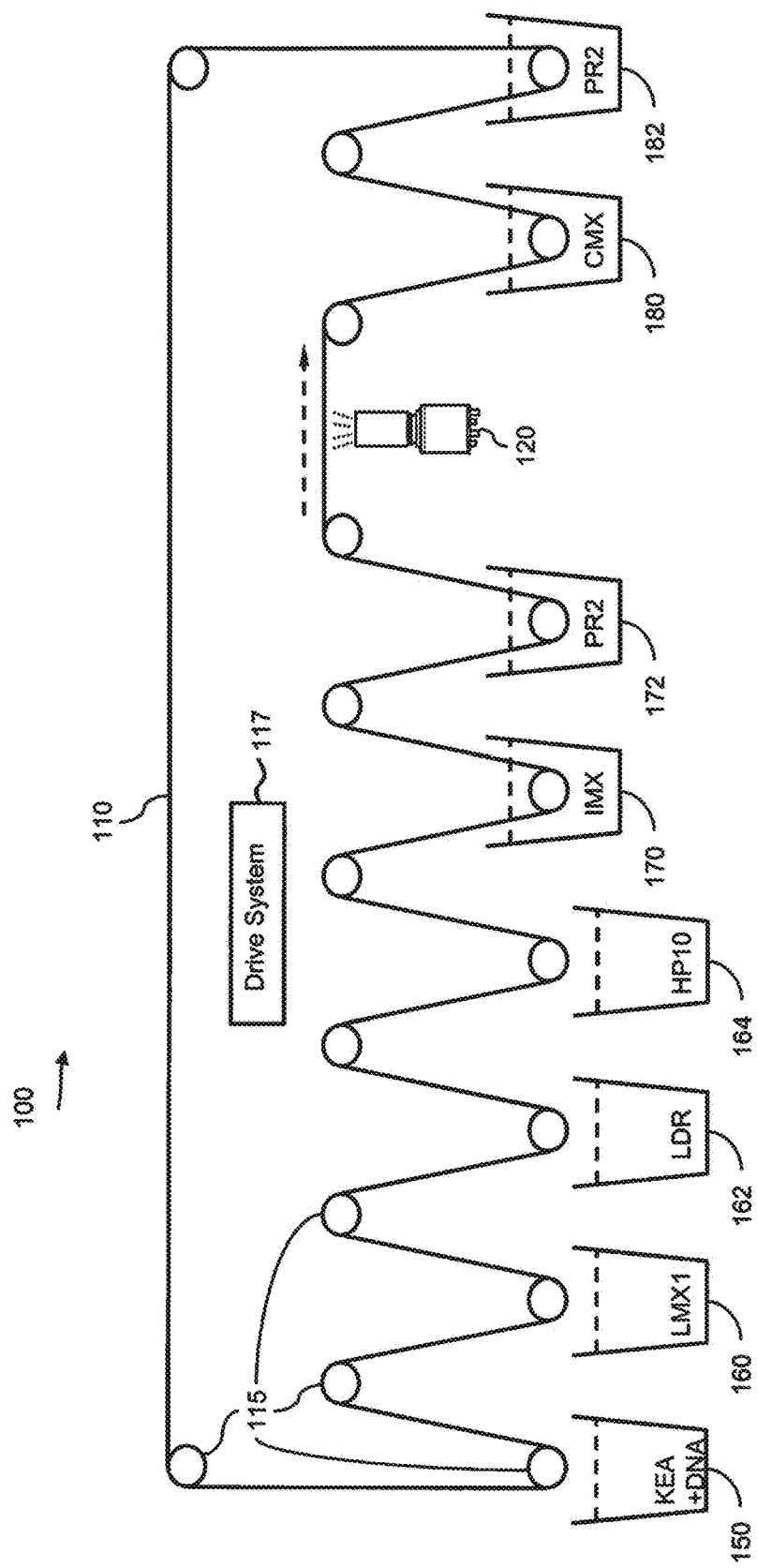
FIG. 6 illustrates plan views of another example of the flexible tape-based chemistry apparatus in a continuous loop configuration in accordance with embodiments herein.
Figure 7:
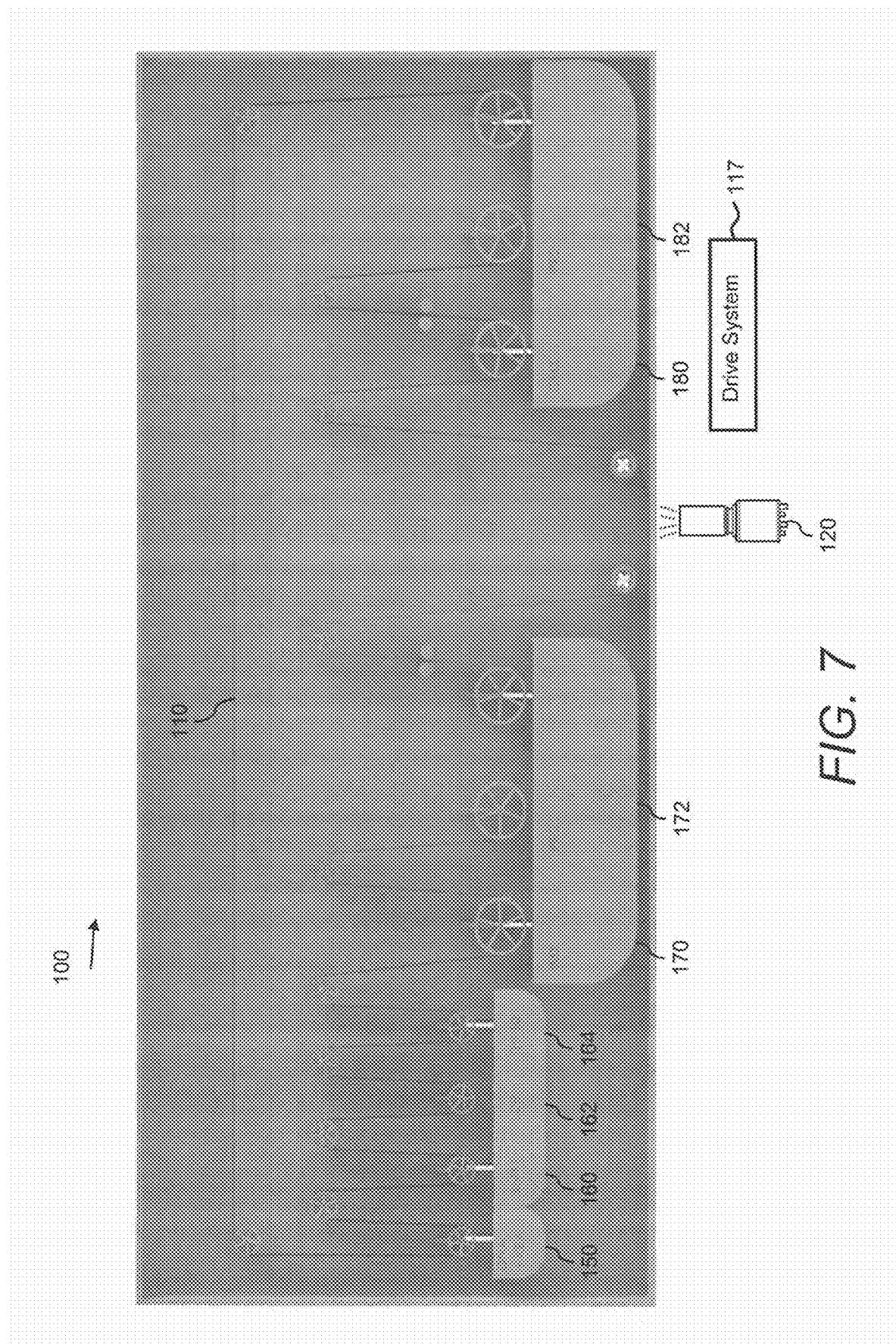
FIG. 7 shows plan views of an example of one instantiation of the flexible tape-based chemistry apparatus shown in FIGS. 3, 4, 5, and 6 in accordance with embodiments herein.

FIGS. 3, 4, 5, and 6 illustrate plan views of another example of flexible tape-based chemistry apparatus 100 in a continuous loop configuration and a process of performing a DNA sequencing operation. In this example, flexible tape-based chemistry apparatus 100 includes eight reservoirs along flexible tape 110 and in relation to certain guide rollers 115 for supporting three modes of operation: (1) cluster generation mode as shown in FIG. 4, (2) read preparation mode as shown in FIG. 5, and (3) sequencing mode as shown in FIG. 6.

The eight reservoirs are provided along flexible tape 110 and in relation to certain guide rollers 115. For example, flexible tape-based chemistry apparatus 100 includes, in order, reservoirs 150, 160, 162, 164, 170, 172, 180, 182. Using reservoirs 150, 160, 162, 164, 170, 172, 180, 182, certain liquids are provided along the path of flexible tape 110, whereby flexible tape 110 may pass selectively in and out of the liquids. Namely, each of the reservoirs 150, 160, 162, 164, 170, 172, 180, 182 is moveable and can be individually controlled. More particularly, when a reservoir is in an "up-position" its respective guide roller 115 (with a certain area of flexible tape 110 riding thereon) is submerged in the liquid in the reservoir. Further, when a reservoir is in a "down-position" its respective guide roller 115 (with a certain area of flexible tape 110 riding thereon) is not submerged in the liquid in the reservoir. For example, FIG. 3 shows all of the reservoirs 150, 160, 162, 164, 170, 172, 180, 182 in the down-position. Therefore, there is no portion of flexible tape 110 submerged. Individually controlled actuators (not shown) are used to move the respective reservoirs to the up-position or down-position.

Further, if reservoirs 150, 160, 162, 164, 170, 172, 180, 182 are provided in order and the movement of flexible tape 110 is in the direction from reservoir 150 toward reservoir 182, read head 120 is arranged between reservoir 172 and reservoir 180 as shown. Namely, read head 120 is arranged downstream of reservoirs 150, 160, 162, 164, 170, 172 and upstream of reservoirs 180, 182.

Referring again to FIG. 3, the contents of reservoirs 150, 160, 162, 164, 170, 172, 180, 182 are as follows. Reservoir 150 is loaded with the sample liquid to be sequenced, such as a mixture of the sample DNA and KEA reagents (or KEA+DNA). Reservoir 160 is loaded with a linearization mix (LMXI), which is used to linearize the strand. Reservoir 162 is loaded with a linearization denaturation reagent (LDR), such as sodium hydroxide (NaOH) to displace one of the DNA strands and leaving a ssDNA molecule on the surface. Reservoir 164 is loaded with a sequencing primer (HP10) from the 3' end of which the sequencing by synthesis (SBS) reaction proceeds. Reservoir 170 is loaded with IMX. Reservoir 172 is loaded with PR2. Reservoir 180 is loaded with CMX. Reservoir 182 is also loaded with PR2.

Referring now to FIG. 4, in a first step, reservoir 150 is in the up-position while reservoirs 160, 162, 164, 170, 172, 180, 182 are in the down-position. Flexible tape-based chemistry apparatus 100 is now in the cluster generation mode of operation. Then, a portion of flexible tape 110 is advanced into reservoir 150 at a certain speed and/or dwell time. In so doing, DNA is clustered on the surface of the portion of flexible tape 110 that is in reservoir 150.

Referring now to FIG. 5, in a next step, reservoirs 160, 162, 164 are in the up-position while reservoirs 150, 170, 172, 180, 182 are in the down-position. Flexible tape-based chemistry apparatus 100 is now in the read preparation mode of operation. Then, the portion of flexible tape 110 that was clustered in FIG. 4 is advanced through reservoirs 160, 162, 164 at a certain speed and/or dwell time. In so doing, the clusters are prepared for sequencing.

Referring now to FIG. 6, in a next step, reservoirs 170, 172, 180, 182 are in the up-position while reservoirs 150, 160, 162, 164 are in the down-position. Flexible tape-based chemistry apparatus 100 is now in the sequencing mode of operation. Then, the portion of flexible tape 110 that was clustered in FIG. 4 is advanced through reservoirs 170, 172, 180, 182 at a certain speed and/or dwell time. In this step, the clusters pass by the field of view of read head 120. Using read head 120, images of the clusters are captured and sequencing information is obtained.

Figure 8:
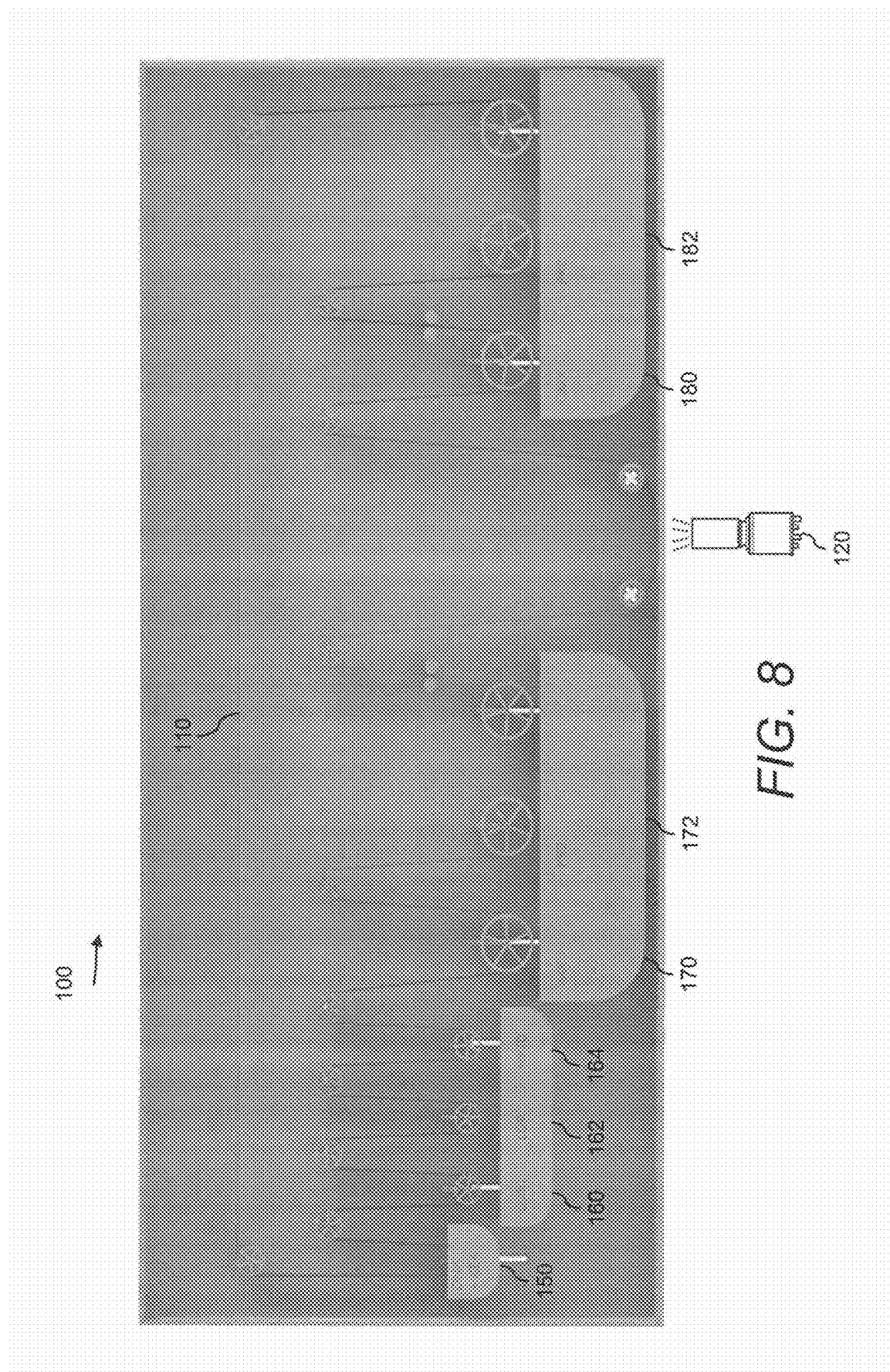
FIG. 8 shows plan views of an example of one instantiation of the flexible tape-based chemistry apparatus shown in FIGS. 3, 4, 5, and 6 in accordance with embodiments herein.
Figure 9:
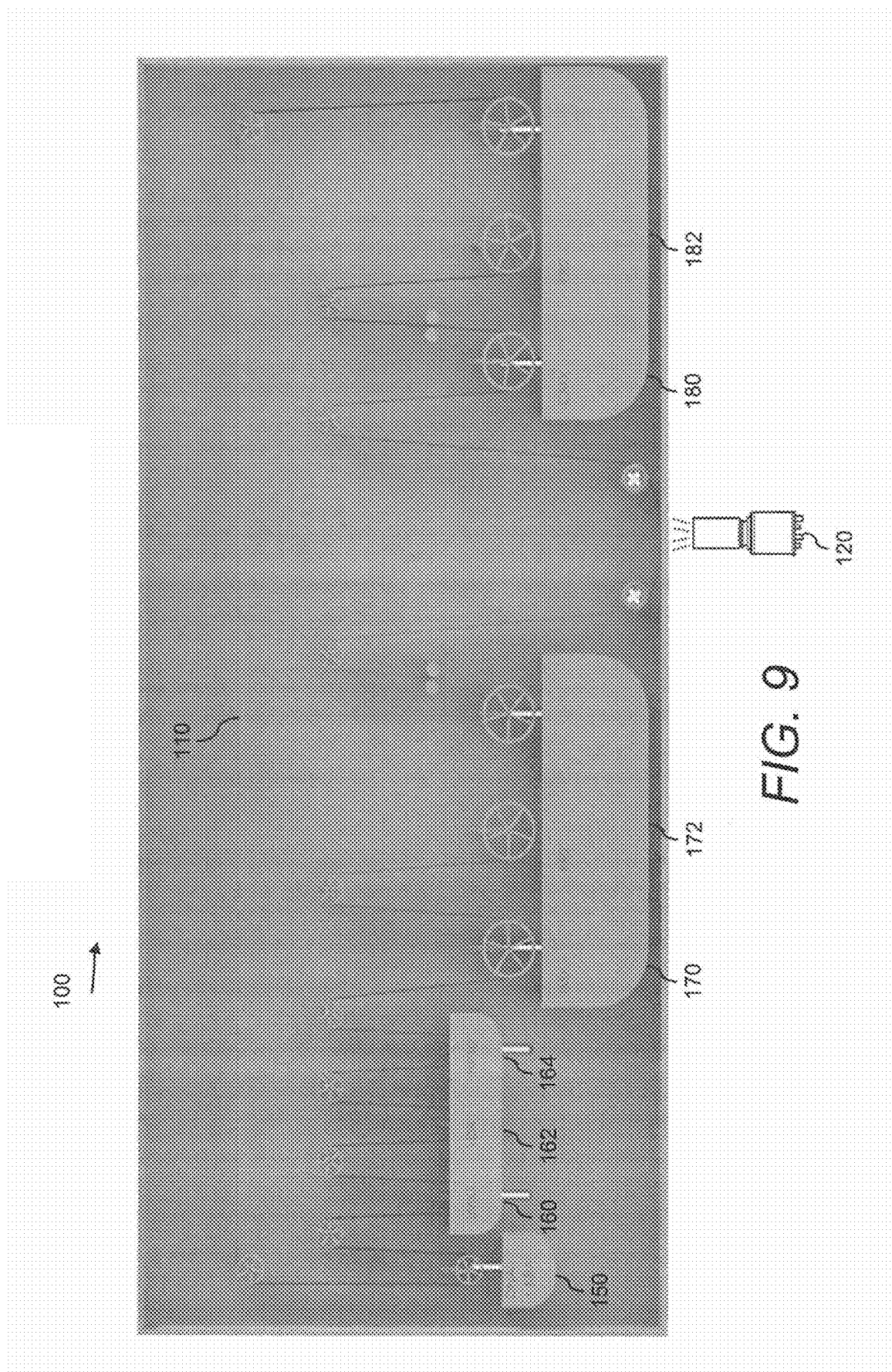
FIG. 9 shows plan views of an example of one instantiation of the flexible tape-based chemistry apparatus shown in FIGS. 3, 4, 5, and 6 in accordance with embodiments herein.
Figure 10:
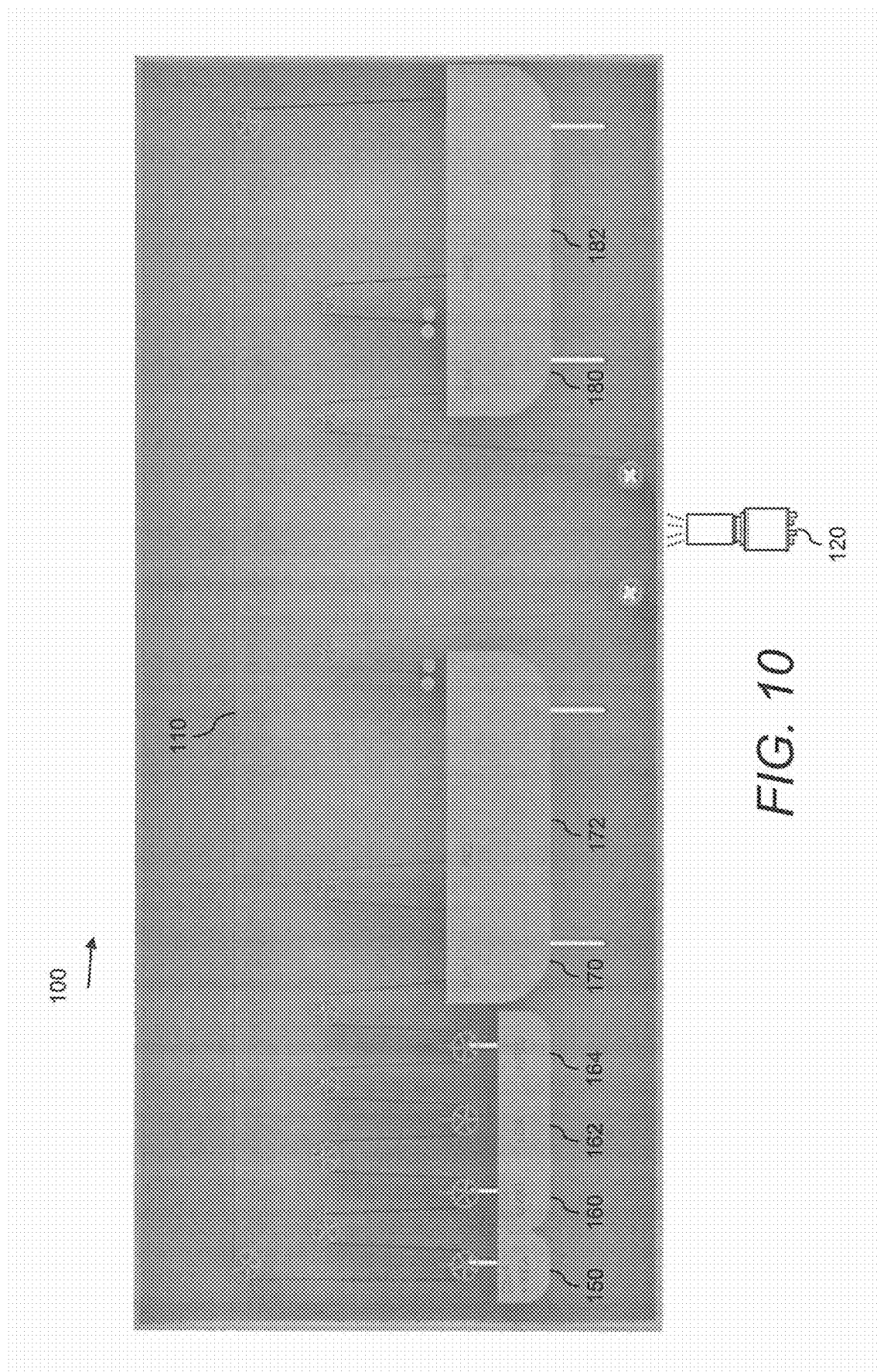
FIG. 10 shows plan views of an example of one instantiation of the flexible tape-based chemistry apparatus shown in FIGS. 3, 4, 5, and 6 in accordance with embodiments herein.

FIGS. 7, 8, 9, and 10 show plan views of an example of one instantiation of flexible tape-based chemistry apparatus 100 shown in FIGS. 3, 4, 5, and 6. Namely, FIG. 7 correlates to FIG. 3, wherein reservoirs 150, 160, 162, 164, 170, 172, 180, 182 are loaded with their respective liquids. FIG. 8 correlates to FIG. 4, which is the cluster generation mode. FIG. 9 correlates to FIG. 5, which is the read preparation mode. FIG. 10 correlates to FIG. 7, which is the sequencing mode.

Figure 11:
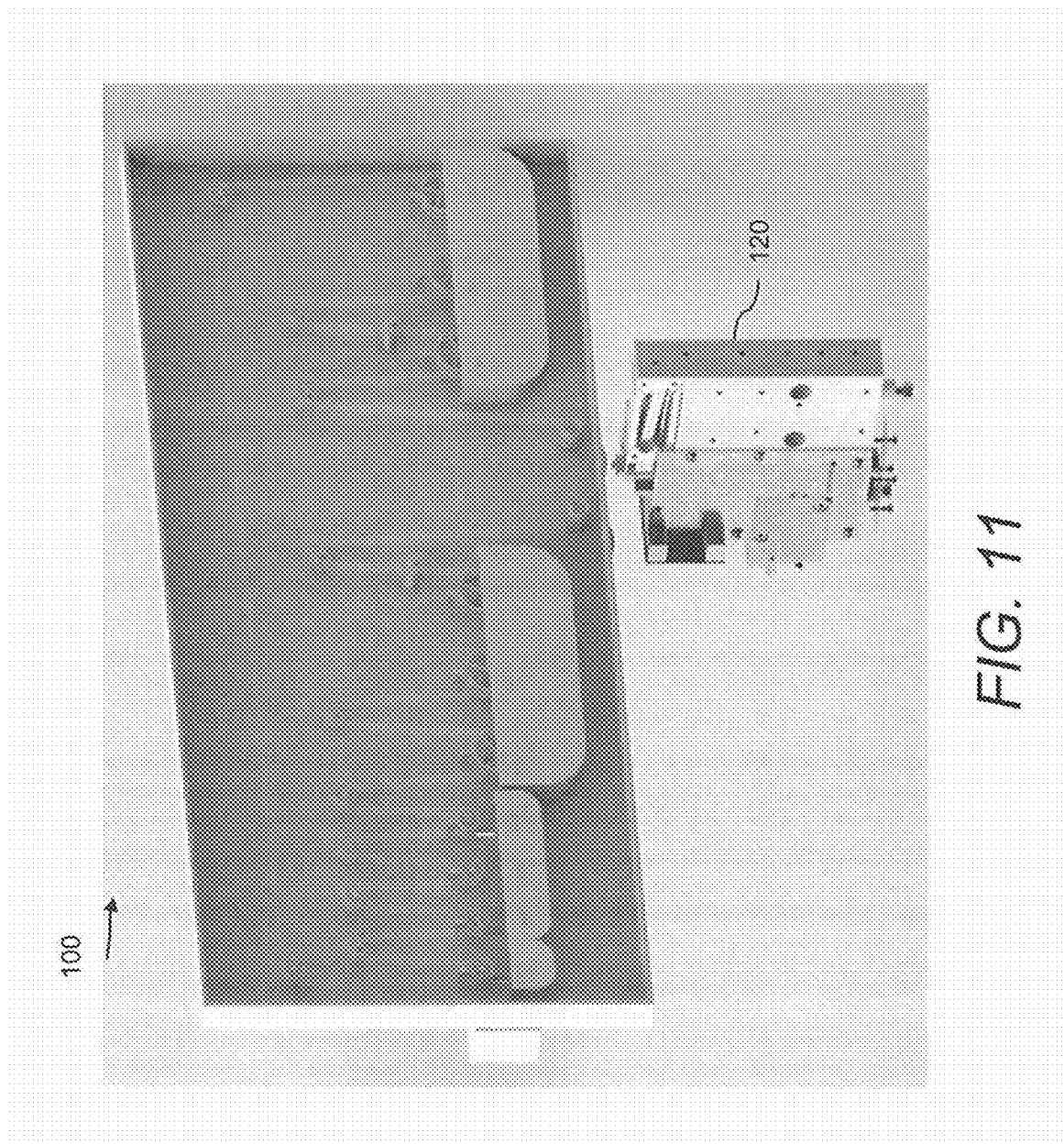
FIG. 11 shows a perspective view of the flexible tape-based chemistry apparatus shown in FIGS. 7, 8, 9, and 10 in accordance with embodiments herein.

FIG. 11 shows a perspective view of flexible tape-based chemistry apparatus 100 shown in FIGS. 7, 8, 9, and 10.

Flexible tape-based chemistry apparatus 100 is not limited to the number and types of reaction sites (i.e., reservoirs) shown in FIGS. 1 through 11. Flexible tape-based chemistry apparatus 100 can support many reaction sites, and can switch between reaction sites to conduct reactions as needed. For example, flexible tape-based chemistry apparatus 100 can include 1, 2, 3, 4, 5, 6, 7, 8, 9, 10, 20, 30, 40, 50, 60, 70, 80, 90, 100 or more reaction sites.

FIG. 12A illustrates a plan view of an example of a configuration of read head 120 of flexible tape-based chemistry apparatus 100. Wherein FIGS. 1 through 11 show read head 120 directed at a flat portion of flexible tape 110, in other configurations read head 120 may be directed at a portion of flexible tape 110 at a guide roller 115. FIG. 12A shows a focal plane 190 passing through a midpoint of the guide roller 115. There a focal point 192 on one side of the guide roller 115 and a focal point 194 on the opposite side of the guide roller 115. FIG. 12B shows an example of an image 196 that was captured using the read head configuration shown in FIG. 12A. Portions of image 196 correlate to focal point 192 and focal point 194.

In other embodiments, instead of flexible tape 110 being held stationary and the reservoirs movable, the reservoirs (e.g., reservoirs 150, 160, 162, 164, 170, 172, 180, 182) are held stationary and guide rollers 115 are movable in order to submerge or not submerge flexible tape 110 into the reservoirs. In this example, particularly for the continuous loop configuration in which flexible tape 110 is a fixed length, guide rollers 115 are provided on idler arms or some kind of slip mechanism for automatically adjusting their collective positions and thus compensate for the movement of flexible tape 110 on any one guide roller 115 that is moved into or out of a reservoir. The idler arms or slip mechanism are used to keep flexible tape 110 taught with guide rollers 115 (e.g., gears) at different positions. For example, the top guide rollers 115 (e.g., gears) can be vertically movable and spring loaded so that they move down when the lower guide rollers 115 (e.g., gears) are pulled down to cause flexible tape 110 to enter the reagents.

In yet other embodiments, flexible tape-based chemistry apparatus 100 shown in FIGS. 3, 4, 5, and 6 and in FIGS. 7, 8, 9, and 10 is a reel-to-reel configuration instead of a continuous loop configuration. Correlating the reel-to-reel configuration to, for example, a standard C90 audio cassette tape, the tape is about 3.81 mm wide and 132 m long. In this example, the area scanned in a standard sequencing run is about 4,424 mm$^2$. The sequencing run "equivalent" length of tape is about 4,424 mm$^2$/3.81 mm, which is 1,161 mm (just over 1 m). For this, 8 genomes can be acquired. Accordingly, a full length C90 tape provides 132/1.161*8=910 human genomes. In other words, 1 human genome requires only about 14.5 cm of tape and can be scanned at 2.4 mm/s at ~60 s/cycle, or for 2×150 cycles=60s×300 cycles=300 minutes or 5 hrs. Therefore, 5 human genomes requires about 72.5 cm of tape, and can be scanned at 12 mm/s (current fastest camera speed) to also give 60 s/cycle time, generating 1 genome/hr over about 5 hrs.

In yet other embodiments, flexible tape 110 can be encoded with certain information. In one example, if flexible tape 110 is magnetic tape, information can be encoded magnetically. In this example, flexible tape-based chemistry apparatus 100 may include a magnetic read head for writing/reading information to/from flexible tape 110. In another example, if flexible tape 110 is plastic tape, information can be encoded using optical markings. In this example, read head 120, which is, for example, a CCD image sensor, may be used to detect the optical markings. Any type of information can be encoded. When using magnetic tape, for example, a magnetic read-write head can be used to identify the region in which the chemistry is taking place (reaction sites) for a variety of purposes. For example, magnetic signals on flexible tape 110 can tell the drive system 117 when to raise and lower the reservoirs for conducting chemistry at various reaction sites—i.e., this can be used to align reaction sites with required reagents. In another example, magnetic signals on flexible tape 110 can tell the drive system 117 when to start detecting at various reaction sites—i.e., this can be used to align reaction sites with required reagents.

In yet other embodiments, both sides of flexible tape 110 can be used. In one example, flexible tape-based chemistry apparatus 100 can include two read heads 120, one for each side of flexible tape 110. In another example, flexible tape 110 can be a Möbius strip. A Möbius strip is a one-sided nonorientable surface obtained by cutting a closed band into a single strip, giving one of the two ends a half twist, and then reattaching the two ends. If using the Möbius strip, only one read head 120 is required because it is one-sided. A benefit of these configurations is that twice as much tape area is now available as compared with using just one side of flexible tape 110.

In yet other embodiments, more elaborate reservoir configurations can be used in flexible tape-based chemistry apparatus 100. For example, instead of a simple reservoir in which the reservoir is in the up-position or down-position, a carousel of reservoirs is provided at the reservoir location. Using the carousel of reservoirs (e.g., a carousel of four reservoirs), reservoirs can be rotating from one to another at that location.

A benefit of the flexible tape-based chemistry apparatuses disclosed herein as compared with, for example, standard flow cell technology is that they require no pumps, no valves, no x-y stages, and the read head does not need to move.

Another benefit of the flexible tape-based chemistry apparatuses disclosed herein as compared with, for example, standard flow cell technology is that they are easily scalable by, for example, using larger area tape. Further, the flexible tape-based chemistry apparatuses can include any number and sets of reagents (i.e., reservoirs) depending on what operations are needed.

In yet other embodiments, flexible tape-based chemistry apparatus 100 shown in FIGS. 3, 4, 5, and 6 and in FIGS. 7, 8, 9, and 10 can include reservoirs that are heated and wherein the heaters can be individually controlled. For example, resistive wire can be embedded into the molded walls of the reservoirs. These wires can be accessed through the back of the apparatus for external control. Thermocouples can also be integrated into the apparatus for monitoring the temperature at each reservoir. Accordingly, yet another benefit of the flexible tape-based chemistry apparatuses disclosed herein as compared with, for example, standard flow cell technology is that they can ensure that reactions take place at the appropriate temperature for the particular reaction occurring in that reservoir. Further, while the reservoirs can be heated, the read operations can take place at ambient temperature, which will greatly improve the accuracy of the sequencing performed.

Yet another benefit of the flexible tape-based chemistry apparatuses disclosed herein as compared with, for example, standard flow cell technology is that they can be used as a random access system, in which reservoirs can drop in and out as desired depending on the operations. For example, different regions of flexible tape 110 can be assigned to different experiments.

Yet another benefit of the flexible tape-based chemistry apparatuses disclosed herein as compared with, for example, standard flow cell technology is that they can have lower reagent requirements as no "flushing" of fNs occurs; reagents can be reused.

Still another benefit of the flexible tape-based chemistry apparatuses disclosed herein as compared with, for example, standard flow cell technology is that they can provide a single consumable, tape-based cartridge containing, for example, a coated/grafted cluster tape, reagent reservoirs (optionally with integrated heaters). The chemistry apparatus also provides the possibility of room temperature imaging, a drive wheel, guide rollers, and actuators to move reservoirs and to switch between modes, e.g., clustering, read preparation, and sequencing. With respect to coating and grafting, coating and grafting of conventional flow cells is costly as it is a relatively serial and labor intensive process, which is difficult to automate. By contrast, coating and grafting large reels of tape for use in flexible tape-based chemistry apparatus 100 described herein may be fairly amenable to mass production with far less labor requirements.

Kinetic Exclusion Amplification (KEA)

In some embodiments, the methods and systems employ kinetic exclusion amplification (KEA), also referred to as exclusion amplification (ExAmp). A nucleic acid library of the present disclosure can be made using the devices of the systems and methods herein that exploit kinetic exclusion. Kinetic exclusion can occur when a process occurs at a sufficiently rapid rate to effectively exclude another event or process from occurring. Take for example the making of a nucleic acid array where sites of the array are randomly seeded with target nucleic acids from a solution and copies of the target nucleic acid are generated in an amplification process to fill each of the seeded sites to capacity. In accordance with the kinetic exclusion methods, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of US Application Pub. No. 2013/0338042, which is incorporated herein by reference in its entirety.

Kinetic exclusion can exploit a relatively slow rate for making a first copy of a target nucleic acid vs. a relatively rapid rate for making subsequent copies of the target nucleic acid or of the first copy. In the example of the previous paragraph, kinetic exclusion occurs due to the relatively slow rate of target nucleic acid seeding (e.g. relatively slow diffusion or transport) vs. the relatively rapid rate at which amplification occurs to fill the site with copies of the nucleic acid seed. In another exemplary embodiment, kinetic exclusion can occur due to a delay in the formation of a first copy of a target nucleic acid that has seeded a site (e.g. delayed or slow activation) vs. the relatively rapid rate at which subsequent copies are made to fill the site. In this example, an individual site may have been seeded with several different target nucleic acids (e.g. several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site.

An amplification reagent can include further components that facilitate amplicon formation and in some cases increase the rate of amplicon formation. An example is a recombinase. Recombinase can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590, each of which is incorporated herein by reference.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, Mass.). Further, examples of useful formulations that include a helicase protein are described in U.S. Pat. Nos. 7,399,590 and 7,829,284, each of which is incorporated herein by reference.

What is claimed is:

1. An apparatus for applying a chemistry to samples of interest, comprising:
   a flexible tape mounted on an arrangement of guide rollers, wherein samples of interest are immobilized to respective local areas along a common solid surface of at least one side of the flexible tape;
   one or more read heads in relation to the flexible tape;
   a plurality of reservoirs along a path of the flexible tape, wherein the reservoirs comprise liquids comprising chemical reagents for performing a select chemistry on the samples of interest immobilized to the respective local areas along the common solid surface of the flexible tape; and
   a drive system for driving at least one of the guide rollers to advance the flexible tape into and out of the reservoirs.

2. The apparatus of claim 1, wherein the flexible tape mounted on the arrangement of guide rollers comprises a continuous loop configuration.

3. The apparatus of claim 1, wherein the flexible tape mounted on the arrangement of guide rollers comprises a reel-to-reel configuration.

4. The apparatus of claim 1, wherein the at least one side of the flexible tape is in direct contact with a flat surface of each of the guide rollers.

5. The apparatus of claim 1, wherein the guide rollers comprise sprockets, and wherein the flexible tape comprises sprocket holes along edges of the flexible tape.

6. The apparatus of claim 1, wherein the one or more read heads are positioned such that the flexible tape is within a field of view of the corresponding read head and such that a plane of the flexible tape is substantially at a focal plane of the corresponding read head.

7. The apparatus of claim 1, wherein the one or more read heads comprise a digital imaging device.

8. The apparatus of claim 7, wherein the digital imaging device comprises a charge-coupled device (CCD) image sensor.

9. The apparatus of claim 1, wherein at least one of the plurality of reservoirs comprises a liquid comprising an incorporation mix.

10. The apparatus of claim 1, wherein at least one of the plurality of reservoirs comprises a liquid comprising a wash buffer.

11. The apparatus of claim 1, wherein at least one of the plurality of reservoirs comprises a liquid comprising a cleavage mix.

12. The apparatus of claim 1, wherein the samples of interest represent clusters of DNA templates, and at least one of the plurality of reservoirs comprises a liquid comprising sample DNA and reagents suitable for conducting kinetic exclusion amplification.

13. The apparatus of claim 1, wherein at least one of the plurality of reservoirs comprises a liquid comprising a linearization mix.

14. The apparatus of claim 1, wherein at least one of the plurality of reservoirs comprises a liquid comprising a linearization denaturation reagent.

15. The apparatus of claim 1, wherein at least one of the plurality of reservoirs comprises a liquid comprising a sequencing primer.

16. The apparatus of claim 1, wherein the reservoirs are moveable and capable of being individually controlled.

17. The apparatus of claim 1, wherein the guide rollers are moveable and capable of being individually controlled.

18. The apparatus of claim 1, wherein at least one read head is arranged downstream of the reservoirs comprising sequencing reagents.

19. The apparatus of claim 1, wherein the flexible tape comprises magnetic tape, plastic tape, or glass.

20. The apparatus of claim 19, wherein the flexible tape comprises magnetic tape and wherein at least one read head is a magnetic read head for at least one of writing information to or reading information from the flexible tape.

21. The apparatus of claim 1, wherein the samples of interest are bound to both sides of the flexible tape, further wherein the apparatus comprises two read heads in which one read head is positioned in relation to one side of the flexible tape and another read head is positioned in relation to another side of the flexible tape.

22. The apparatus of claim 1, wherein samples of interest are bound to one side of the flexible tape, and wherein the flexible tape comprises a Möbius strip.

23. The apparatus of claim 1, wherein the plurality of reservoirs comprises a carousel of reservoirs capable of rotating from one to another at a given location.

24. The apparatus of claim 1, wherein at least one of the plurality of reservoirs comprises an independently controlled heating element.

25. A method of DNA template cluster generation using the apparatus of claim 1 comprising:
providing the flexible tape mounted on the arrangement of guide rollers, wherein the samples of interest include clusters of DNA;
arranging the reservoirs along the path of the flexible tape, wherein the chemical reagents are selected for performing DNA sequencing on the DNA templates; and
selectively advancing a portion of the flexible tape into one or more of the reservoirs;
wherein DNA templates are clustered on the flexible tape.

26. A method of DNA template linearization using the apparatus of claim 1 comprising:
providing the flexible tape mounted on the arrangement of guide rollers, wherein the samples of interest include clusters of DNA templates;
arranging the reservoirs along the path of the flexible tape, wherein the chemical reagents for performing DNA sequencing on the DNA templates; and
selectively advancing a portion of the flexible tape into reservoirs, wherein the portion of the flexible tape is advanced sequentially into reservoirs comprising:
a linearization mix;
a linearization denaturation reagent; and
a sequencing primer;
wherein DNA templates on a surface of the portion of the flexible tape are linearized.

27. A method of applying a chemistry to samples of interest using the apparatus of claim 1 comprising:
providing the flexible tape mounted on the arrangement of guide rollers;
arranging the reservoirs along the path of the flexible tape, wherein the chemical reagents are configured for performing a select chemistry on the samples of interest; and
selectively advancing a portion of the flexible tape of the apparatus comprising the samples of interest into reservoirs, wherein the portion of the flexible tape is advanced sequentially into reservoirs comprising:
an incorporation mix;
a wash buffer;
a cleavage mix; and
a wash buffer;
wherein the portion of the flexible tape comprising the samples of interest is passed by a field of view of a read head, wherein images of the samples of interest are captured.

28. The apparatus of claim 1, wherein the select chemistry constitutes a sequencing-by-synthesis (SBS) chemistry.

29. The apparatus of claim 1, wherein the flexible tape is configured to be at least one of submerged and advanced through at least one of the reservoirs at a designated speed or submerged and dwell within at least one of the reservoirs for a designated period of time.

30. An apparatus for applying a chemistry to samples of interest, comprising:
a flexible tape mounted on an arrangement of guide rollers, wherein samples of interest are immobilized to respective local areas along a common solid surface of at least one side of the flexible tape;
one or more read heads in relation to the flexible tape;
a plurality of reservoirs along a path of the flexible tape, wherein the reservoirs comprise liquids comprising chemical reagents for performing a select chemistry on the samples of interest immobilized to the respective local areas along the common solid surface of the flexible tape; and
a drive system for driving at least one of the guide rollers to advance the flexible tape into and out of the reservoirs;
wherein at least one of the guide rollers is configured to be submerged within one of the reservoirs as the flexible tape is advanced through the one reservoir.

* * * * *

UNITED STATES PATENT AND TRADEMARK OFFICE
CERTIFICATE OF CORRECTION

PATENT NO. : 10,351,846 B2
APPLICATION NO. : 14/851090
DATED : July 16, 2019
INVENTOR(S) : Jonathan Mark Boutell, Gary Mark Skinner and Gareth Jenkins Page 1 of 1

It is certified that error appears in the above-identified patent and that said Letters Patent is hereby corrected as shown below:

On the Title Page

Insert item [30]:
--Foreign Application Priority Data
Sep. 17, 2014 (UK)........1416422.2--

Signed and Sealed this
Fifteenth Day of October, 2019

Andrei Iancu
*Director of the United States Patent and Trademark Office*